United States Patent
Ding

(10) Patent No.: US 7,822,251 B2
(45) Date of Patent: Oct. 26, 2010

(54) VARIATIONAL APPROACH ON WHOLE BODY SPECT/CT REGISTRATION AND ZIPPING

(75) Inventor: Xinhong Ding, Buffalo Grove, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 1001 days.

(21) Appl. No.: 11/605,992

(22) Filed: Nov. 29, 2006

(65) Prior Publication Data

US 2008/0125639 A1    May 29, 2008

(51) Int. Cl.
*G06K 9/00*    (2006.01)
*A61B 5/05*    (2006.01)

(52) U.S. Cl. .................... 382/130; 600/407

(58) Field of Classification Search ............ 382/128, 382/129, 130, 131, 132, 133, 134, 151, 294; 378/4, 8, 21–27, 101, 901; 600/407, 410, 600/411, 425; 128/920, 922
See application file for complete search history.

(56) References Cited

U.S. PATENT DOCUMENTS

| | | | | |
|---|---|---|---|---|
| 6,684,098 B2* | 1/2004 | Oshio et al. | ........... | 600/429 |
| 6,909,794 B2* | 6/2005 | Caspi | ........... | 382/128 |
| 7,254,438 B2* | 8/2007 | DeSilets et al. | ........... | 600/427 |
| 7,323,690 B2* | 1/2008 | Lusser et al. | ........... | 250/363.04 |
| 7,412,027 B2* | 8/2008 | Yakubovsky et al. | ........... | 378/63 |

* cited by examiner

*Primary Examiner*—Abolfazl Tabatabai
(74) *Attorney, Agent, or Firm*—Peter Kendall

(57) ABSTRACT

A method and a system for implementing the method for simultaneously registering and zipping a multiple scan whole body SPECT/CT image. The method includes the steps of simultaneously registering and zipping multiple input images and re-sampling the registered images. The step of simultaneously registering and zipping multiple input images is accomplished by initially aligning the images to be registered with each other, aligning the images with a reference image, and adjusting the alignment of the images with each other.

19 Claims, 3 Drawing Sheets

VARIATIONAL APPROACH ON WHOLE BODY SPECT/CT REGISTRATION AND ZIPPING

BACKGROUND DESCRIPTION

1. Technical Field

This invention relates generally to SPECT and CT imaging. Specifically, it relates to registering SPECT images and CT images of the same patient regions, and "zipping" together SPECT images of different portions of a whole body scan to provide a single whole body image.

2. Background of the Invention

When taking whole body Single Photon Emission Computed Tomography ("SPECT") and Computed Topography ("CT") scans, in many machines the detector's field of view ("FOV") is limited. It is therefore often necessary to take several separate scans for SPECT, which overlap in the z direction (see FIG. 1), at two or more different positions with respect to a patient. These separate scans must then be "zipped" or appended together after reconstruction.

When such zipping takes place, it is usually impossible to determine the proper zipping position in the overlapping region where zipping occurs, in the z direction (see FIG. 1). When two adjacent images are so overlapped, the proper dividing line could be anywhere in the overlapping region. Presently there are no satisfactory methods to determine this position and to zip the two images together based either on relative bed positions or on image positions.

Even in cases where the zipping position can be approximated, i.e. when the full reconstruction range is used in the overlapping region, other factors may hinder a satisfactory zipped whole body image. These factors may include: bed deflection, patient motion, and image edge handling in 3D reconstruction algorithms with CT attenuation correction.

In many current methods, image registration (i.e., between the SPECT and CT images) and zipping (i.e., of two SPECT images of overlapping adjacent patient regions) are done completely separately. Auto-zipping is done after the multiple whole body SPECT images have been individually registered with the CT image. The separate registration and zipping processes do not generate satisfactory whole body images.

To solve these problems, it is desired to merge the registration task and the zipping task into a single optimization task.

SUMMARY OF THE INVENTION

Therefore, according to the present invention a method for simultaneously registering and zipping a multiple scan whole body SPECT/CT image is provided. The method includes the steps of (a) simultaneously registering and zipping multiple input images and (b) re-sampling the registered images. The step of simultaneously registering and zipping multiple input images is accomplished by (i) initially aligning the images to be registered with each other, (ii) aligning the images with a reference CT image, and (iii) adjusting the alignment of the images with each other.

In order to determine the best registration, which is used to generate a registered output, the method uses the equation:

$$M_{total}(\phi) := \Sigma_j M(U, V_j \circ \phi_j) = \max,$$

which is subject to $$V_{total}(\phi) := \Sigma_{i \neq j} \nu(V_i \circ \phi_i, V_j \circ \phi_j) = \min$$

where U is a CT reference image, V is a set of SPECT images, and $\phi$ is a transform.

Further provided is a system for implementing the method that includes a SPECT/CT scanning device, a processor that receives scans from the SPECT/CT scanning device, and software that inputs multiple images, simultaneously registers and zips the images and outputs a single, unified, registered image.

BRIEF DESCRIPTION OF THE DRAWINGS

The invention will now be described in greater detail in the following by way of example only and with reference to the attached drawings, in which.

DETAILED DESCRIPTION OF THE INVENTION

As required, disclosures herein provide detailed embodiments of the present invention; however, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention.

Figure 1:
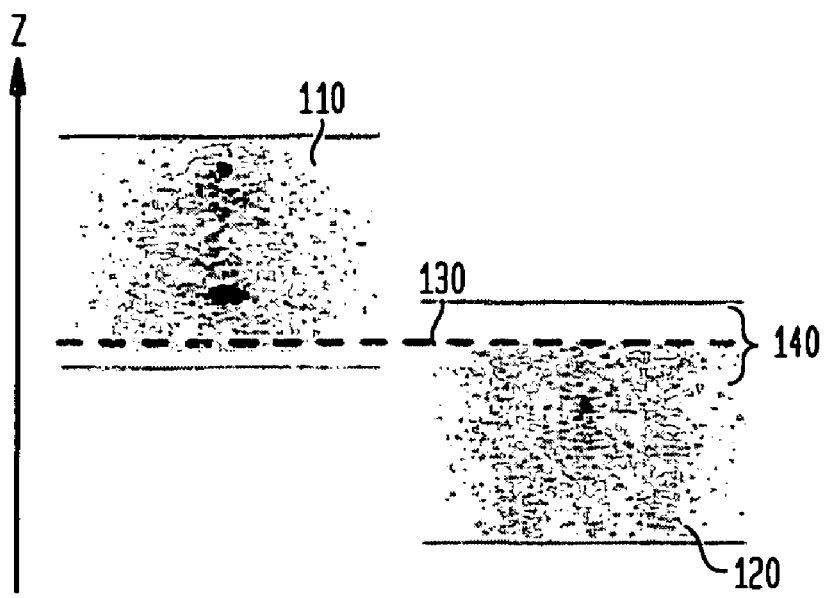
FIG. 1 is an example of two SPECT scans with an overlapping region.
Figure 2:
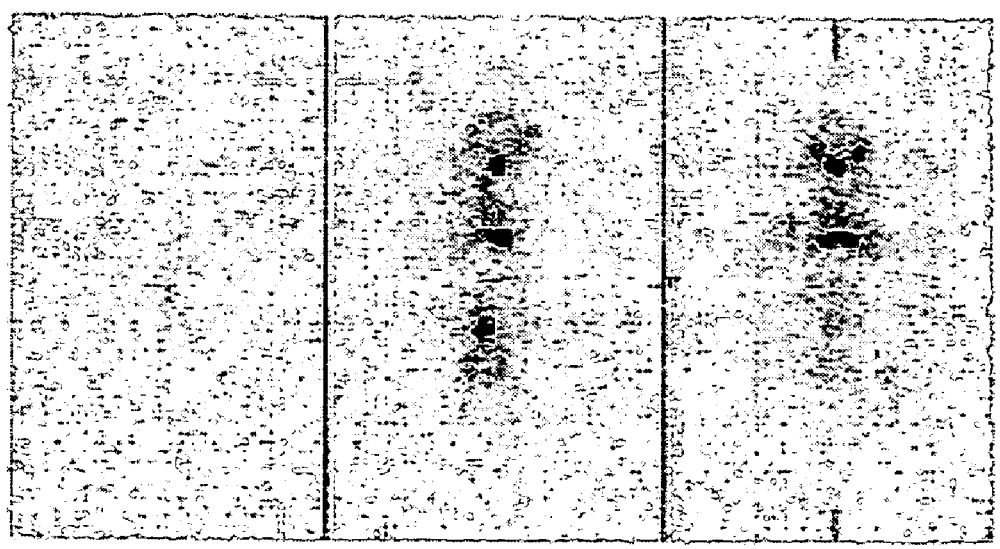
FIG. 2 is an example of unsatisfactory whole body zipping for two SPECT scans.

FIG. 1 depicts two whole body SPECT scans 110 and 120 of overlapping adjacent regions of a patient, where the solid lines represent the image reconstruction range for each image. It is desirable to zip these two SPECT scans 110 and 120 together to create one image. The two SPECT scans 110 and 120 will be zipped together somewhere in the overlapping region 140. However, the proper dividing line 130 could be anywhere in the overlapping region 140. If the wrong dividing line 130 is chosen, an unsatisfactory final image will be produced (see FIG. 2).

Figure 3:
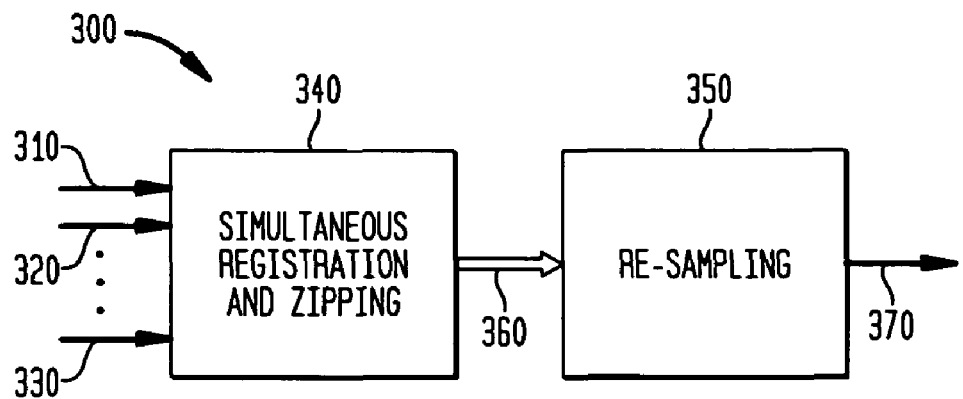
FIG. 3 is a diagram of the method for simultaneously registering and zipping a multiple scan whole body SPECT/CT image

FIG. 3 diagrams the method 300 according to one embodiment of the present invention, which may find the proper dividing line 130 from which to zip the SPECT images together to form a single whole body image. The two main processes in the method 300 are (1) simultaneous registration and zipping (340) and (2) re-sampling (350). The simultaneous registration and zipping 340 may include imputing a reference CT image 310 and imputing whole body SPECT scans 1 (320) through K (330). The simultaneous registration and zipping 340 may not only determine the best alignment (registration) between each individual SPECT image 320 through 330 and the reference CT image 310, but also may determine the best alignment among the K SPECT images 320 through 330 themselves. After the simultaneous registration and zipping 340 is complete, the registered multiple images 360 may be re-sampled in process 350. The re-sampling 350 may sample the multiple registered images 360 (which may have overlaps) to generate a single unified output 370.

Figure 4:
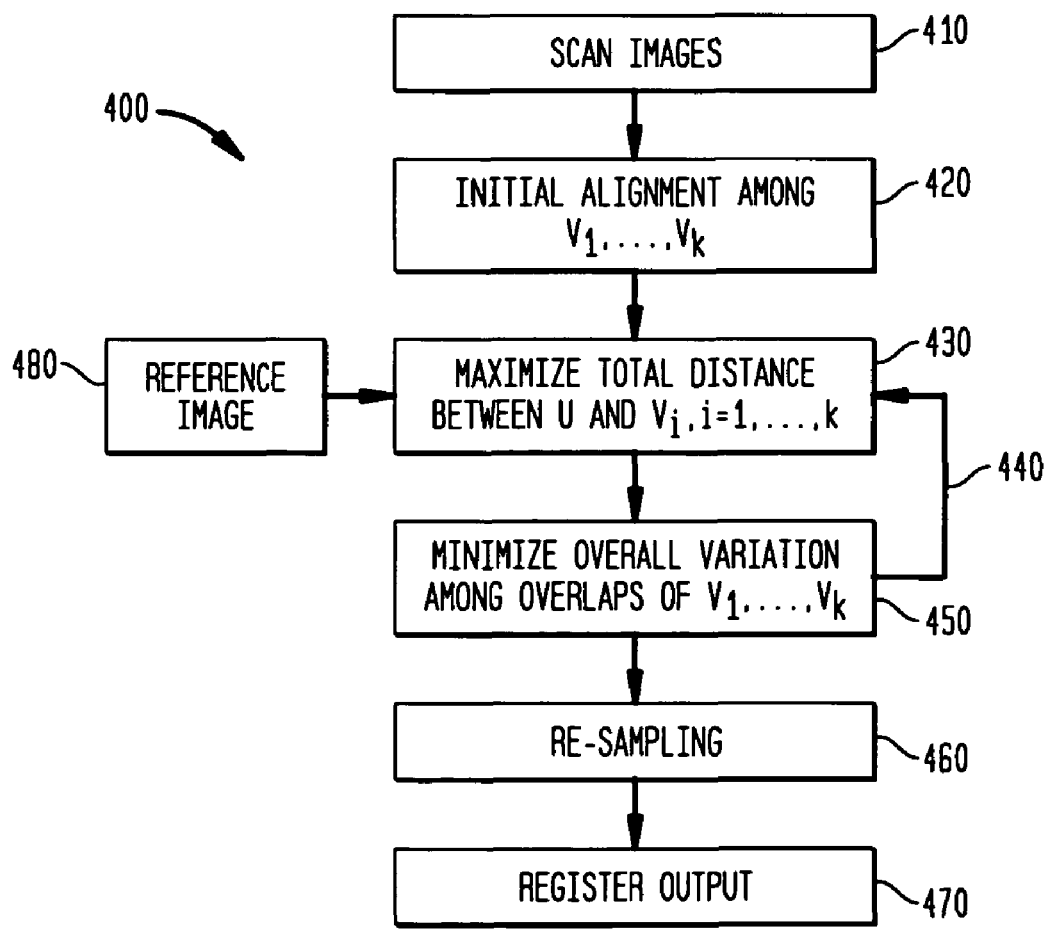
FIG. 4 is a diagram of an algorithm for executing the method.

FIG. 4 depicts an algorithm 400 for completing the method 300. The algorithm may consist of the steps of (1) scanning the SPECT images ("$V_1, \ldots, V_K$") 410, (2) finding an initial alignment among $V_1, \ldots, V_K$ images 420, (3) imputing a reference CT image ("U") 480, (4) maximizing the total distance between U 480 and each SPECT image ("$V_i$") 430, (5) minimizing the overall variation among overlaps of $V_1, \ldots, V_K$ 450 (6) repeating (440) the maximizing 430 and minimizing 450 steps until the best registration is found, (6) re-sampling 460, and (7) registering an output 470.

Finding the initial alignment of the K images $V_1, \ldots, V_K$ 420 may be done based on either bed positions or image positions of the K images. The maximizing 430 and minimizing 450 steps may be formulated as an optimization problem as follows.

Let $R^3$ denote the usual three-dimensional Euclidian space. An image may be defined as a function from $R^3$ to R which satisfies certain regularity conditions. Given two images U and V, where U is a reference image and V is the image to be registered towards U, the objective of the registration between these two images is to find a proper transformation $$\phi: R^3 \to R^3$$

such that U and $V \circ \phi$ are best matched in accordance with a certain objective measure, where $V \circ \phi$ denotes the registered version of V with $V \circ \phi(x) = V(\phi(x))$ for $x \in R^3$.

In a multiple input registration and zipping setting, there may be one reference image U (the CT image) and a set of K SPECT images $\{V_j\}$ to be registered (the multiple whole body SPECT images). It may be necessary to find K best transformations $\{\phi_j\}$ under certain optimization criteria, where each $\phi_j$ represents the best registration between U and $V_j$. The set of functions $\{\phi_j\}$ cannot be found separately because their domains have overlaps in general, and those are the regions where transformations need to be adjusted to make the best zipping for the neighboring two images.

If $\phi = (\phi_1, \ldots, \phi_K)$, the maximizing (430) and minimizing (450) steps may be formulated as an optimization problem as follows:

Given one reference image $U: R^3 \to R^3$ and a set of K images $\{V_j\}$ to be registered, where $V_j: R^3 \to R^3$, $j=1, \ldots, K$, find a transformation $\phi$ such that $$M_{total}(\phi) := \Sigma_j M(U, V_j \circ \phi_j) = \max$$

subject to $$V_{total}(\phi) := \Sigma_{i \neq j} v(V_i \circ \phi_i, V_j \circ \phi_j) = \min \quad (1)$$

where $M(U, V_j \circ \phi_j)$ measures the similarity between the reference image U and the transformed image $V_j \circ \phi_j$; $M_{total}$ is the sum of all $M(U, V_j \circ \phi_j)$; $v(V_i \circ \phi_i, V_j \circ \phi_j)$ measures the variation between the two registered images $V_i \circ \phi_i$ and $V_j \circ \phi_j$ at their overlapped region; and $V_{total}$ is the sum of all $v(V_i \circ \phi_i, V_j \circ \phi_j)$.

One implementation for the optimization of problem (1) is to set the objective functional as $$J(\phi) := -M_{total}(\phi) + \lambda V_{total}(\phi) \quad (2)$$

and search for $\phi^*$ such that $J(\phi^*) = \min$, where $\lambda$ is a constant to be determined. A gradient based steepest descent method may be used to seek the minimum of the functional. First the gradient $\nabla J(\phi)$ may be calculated, and then updates in the search for the optimal transformation $\phi$ may be made according to $$\phi_{n+1} = \phi_n - \mu \nabla J(\phi_n), \mu > 0, n = 1, 2, 3, \ldots$$

where $\mu$ is a constant used to control the convergence rate.

Thus, this registration algorithm searches for the best registration $\phi$ between the set of images $\{V_j\}$ and the reference image U in such a way that the individual images $V_j (1 \leq j \leq K)$ are optimally aligned with respect to the reference image U (in the sense of $M_{total} = \min$).

Once the best registration $\phi$ has been found, it may be used in the final re-sampling operation to generate a registered output. Note that in the conventional image registration setting where the re-sample is based on one transformation function $\phi$ only, the multiple input re-sample algorithm in this operation must handle the multiple transformation functions $\{\phi_j\}$. In particular, interpolation is needed in the overlapped domain of the functions.

Often some type of regularization is needed because the image registration problem is ill-posed.

Let the transformation function $\phi: R^3 \to R^3$ be the deformation map defined by $$\phi(x) = x + u(x)$$

where u is a proper function from $R^3$ to $R^3$.

For the similarity measure M between two images U and V, one may use the popular mutual information defined by $$M(U, V) = \int_{R^3 \times R^3} p_{U,V}(u, v) \log \frac{p_U(u) p_V(v)}{p_{U,V}(u, v)} d(u, v)$$

where $p_U$ and $p_V$ are the probability densities of the pixel values of the images U and V, respectively; $p_{U,V}$ is the joint probability density of the pixel values of images U and V.

For the variation measure v between two overlapped images F and G, one can use the sum of the squared difference defined by $$v(F, G) = \int_O (F(x) - G(x))^2 dx$$

where O denotes the overlapped region between the two images.

Under these notation, equation (1) can be formulated as the following variational problem:

$$\text{minimize } J(u_1, \ldots, u_k) + rS(u_1, \ldots, u_k) \quad (3)$$

where J is defined as in equation (2), S is a regularization term, and $r > 0$ is a regularization parameter. In many cases, the regularization term S can be defined as a bi-linear form of B:

$$S(u_1, \ldots, u_k) = \Sigma_{j=1}^K \int_D \langle B(u_j), B(u_j) \rangle dx, D \subset R^3$$

where B is a differential operator, and $\langle , \rangle$ denotes the inner product in $L_2(R^3)$. $L_2(R^3)$ is the completion of the continuous functions with respect to the $L_2$-norm. For example, for elastic registration, the integral term in the above expression can be represented as $$\int_D \langle B(u_j), B(u_j) \rangle dx = \int_D \left\{ \frac{\alpha}{4} \sum_{i,j=1}^3 (\partial_{x_i} u_j + \partial_{x_j} u_i)^2 + \frac{\beta}{2} (\nabla \cdot u)^2 \right\} dx$$

where $\alpha$ and $\beta$ are the so-called Lamé constants, and $\nabla \cdot$ is the divergence operator. Note that u is the function used to define the non-rigid transformation function $\phi(x) = x + u(x)$. In a multiple input registration setting, with K input images to be registered, there should be K such u's.

Using a proper discretization technique, the regularized minimization problem can be implemented as an iterative algorithm.

Figure 5:
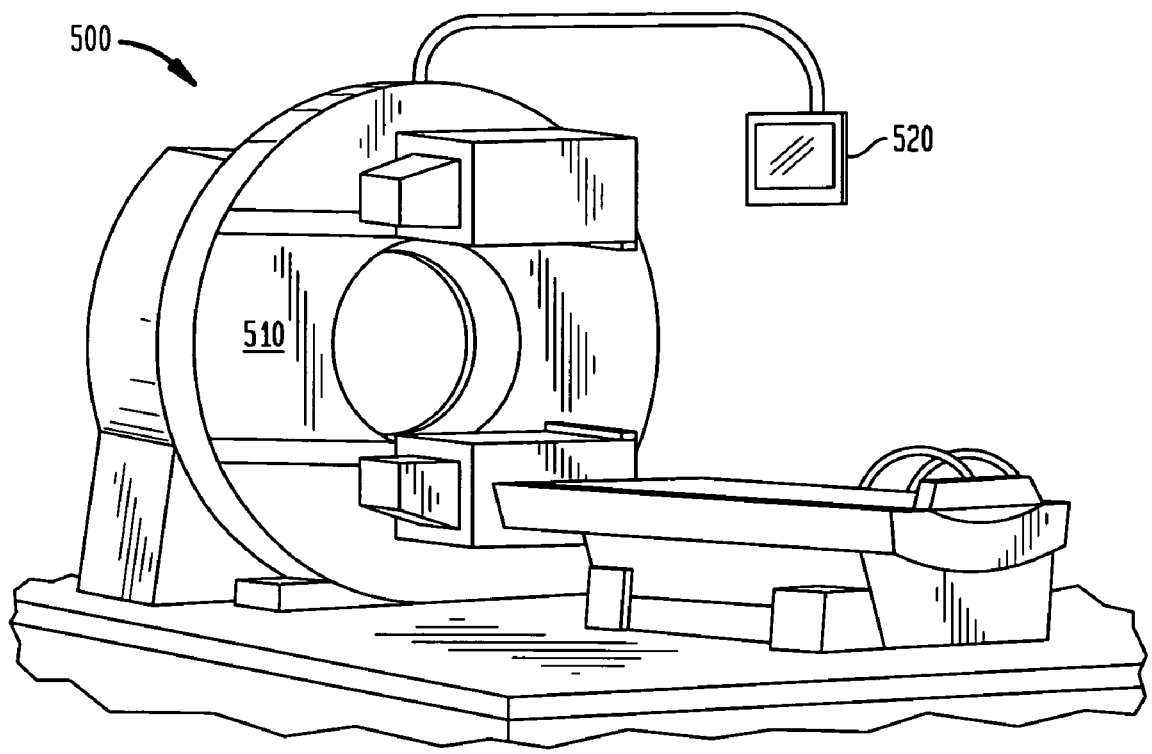
FIG. 5 is a system for simultaneously registering and zipping a multiple scan whole body SPECT/CT image.

FIG. 5 shows an example system 500 that uses the method 300. The system may be comprised of a SPECT/CT scanning device 510 and a processing device. The processing device may obtain scanned images from the scanning device 510 and may run software that implements the algorithm 400 to output a single registered and zipped whole body image. The system may include a monitor 520 for displaying data, operating instructions, etc. from the processing device.

What is claimed is:

1. A method for simultaneously registering and zipping a multiple scan non-whole body SPECT image with a whole body CT image of a same region, comprising:
   (a) initially aligning multiple non-whole body input SPECT images with each other;
   (b) separately aligning each of said multiple non-whole body input SPECT images with said whole body CT image;
   (c) adjusting alignment between said multiple non-whole body input SPECT images based on alignment with said whole body CT image; and
   (d) re-sampling the registered images to obtain a single output zipped image.

2. The method of claim 1, wherein step (a) includes:
   (i) initially aligning the images to be registered with each other;
   (ii) aligning the images with a reference image; and
   (iii) adjusting the alignment of the images with each other.

3. The method of claim 2, wherein step (i) is based on bed positions.

4. The method of claim 2, wherein step (i) is based on image positions.

5. The method of claim 2, wherein the reference image is a CT.

6. The method of claim 2, wherein steps (ii) and (iii) are repeated until a final alignment has been attained.

7. The method of claim 6, wherein steps (ii) and (iii) are accomplished by finding a transformation $\Phi$ wherein:

$$M_{total}(\phi) := \Sigma_j M(U, V_j \circ \phi) = \max$$

subject to $$V_{total}(\phi) := \Sigma_{i \neq j} v(V_i \circ \phi_i, V_j \circ \phi_j) = \min$$

wherein:
   $M(U, V_j \circ \phi_j)$ measures the similarity between the reference image U and the transformed image $V_j \circ_j$;
   $M_{total}$ is the sum of all $M(U, V_j \circ \phi_j)$;
   $v(V_i \circ \phi_i, V_j \circ \phi_j)$ measures the variation between the two registered images $V_i \circ \phi_i$ and $V_j \circ \phi_j$ at their overlapped region; and
   $V_{total}$ is the sum of all $v(V_i \circ \phi_i, V_j \circ \phi_j)$.

8. The method of claim 7, wherein the transformation $\phi$ is found by searching for a $\phi^*$ such that $J(\phi^*)=\min$ using the equation:

$$J(\phi) := -M_{total}(\phi) + \lambda V_{total}(\phi)$$

wherein:
   $\lambda$ is a constant to be determined.

9. The method of claim 8, wherein $\phi^*$ is found by calculating the gradient $\nabla J(\phi)$ and updating the search for the optimal transformation $\phi$ according to:

$$\phi_{n+1} = \phi_n - \mu \nabla J(\phi_n), \mu > 0, n = 1, 2, 3, \ldots$$

wherein:
   $\mu$ is a constant used to control the convergence rate.

10. The method of claim 7, wherein the transformation $\phi$ (for $\phi(x)=x+u(x)$) is found by minimizing:

$$J(u_1, \ldots, u_k) + rS(u_1, \ldots, u_k)$$

wherein:

$$J(\phi) := -M_{total}(\phi) + \lambda V_{total}(\phi)$$

wherein, $\lambda$ is a constant to be determined;
S is a regularization term; and
$r>0$ is a regularization parameter.

11. The method of claim 10, wherein:

$$S(u_1, \ldots, u_k) = \Sigma_{j=1}^{K} \int_D <B(u_j), B(u_j)> dx, D \subset R^3$$

wherein:
   B is a differential operator; and
   $<,>$ denotes the inner product in $L_2(R^3)$;
   wherein $L_2(R^3)$ is the completion of the continuous functions with respect to the $L_2$-norm.

12. The method of claim 1, further comprising:
   (c) generating a registered output.

13. A system for simultaneously registering and zipping multiple scan whole body SPECT/CT images, comprising:
   a SPECT/CT scanning device;
   a processor in communication with the SPECT/CT scanning device; and
   software executing on the processor, wherein the software
   initially aligns multiple non-whole body input SPECT images with each other;
   separately aligns each of said multiple non-whole body input SPECT images with the whole body CT image
   adjusting alignment between the multiple non-whole body input SPECT images based on alignment with the whole body CT image; and
   re-samples the registered images to obtain a single output zipped image.

14. The system of claim 13, wherein the software:
   initially aligns the images to be registered with each other;
   aligns the images with a reference image; and
   adjusts the alignment of the images with each other.

15. The system of claim 14, wherein the software finds a transformation $\phi$ wherein:

$$M_{total}(\phi) := \Sigma_j M(U, V_j \circ \phi_j) = \max$$

subject to $$V_{total}(\phi) := \Sigma_{i \neq j} \mu(V_i \circ \phi_i, V_j \circ \phi_j) = \min$$

wherein:
   $M(U, V_j \circ \phi_j)$ measures the similarity between the reference image U and the transformed image $V_j \circ_j$;
   $M_{total}$ is the sum of all $M(U, V_j \circ \phi_j)$;
   $v(V_i \circ \phi_i, V_j \circ \phi_j)$ measures the variation between the two registered images $V_i \circ \phi_i$ and $V_j \circ \phi_j$ at their overlapped region; and
   $V_{total}$ is the sum of all $v(V_i \circ \phi_i, V_j \circ \phi_j)$.

16. The system of claim 15, wherein the software finds the transformation $\phi$ by searching for a $\phi^*$ such that $J(\phi^*)=\min$ using the equation:

$$J(\phi) := M_{total}(\phi) + \lambda V_{total}(\phi)$$

wherein:
   $\lambda$ is a constant to be determined.

17. The method of claim 16, wherein the software finds $\phi^*$ by calculating the gradient $\nabla J(\phi)$ and updating the search for the optimal transformation $\phi$ according to:

$$\phi_{n+1} = \phi_n - \mu \nabla J(\phi_n), \mu > 0, n = 1, 2, 3, \ldots$$

wherein:
   $\mu$ is a constant used to control the convergence rate.

18. The system of claim 15, wherein the software finds transformation φ (for $\phi(x)=x+u(x)$) by minimizing:

$$J(u_1,\ldots,u_k)+rS(u_1,\ldots,u_k)$$

wherein:

$$J(\phi):=-M_{total}(\phi)+\lambda V_{total}(\phi);$$

wherein, λ is a constant to be determined;
S is a regularization term; and
r>0 is a regularization parameter.

19. The system of claim 18, wherein:

$$S(u_1,\ldots,u_k)=\sum_{j=1}^{K}\int_D <B(u_j,B(u_j)>dx, D\subset R^3$$

wherein:
B is a differential operator; and
<,> denotes the inner product in $L_2(R^3)$;
wherein $L_2(R^3)$ is the completion of the continuous functions with respect to the $L_2$-norm.

* * * * *